(12) United States Patent
Van Der Weide

(10) Patent No.: US 11,433,251 B2
(45) Date of Patent: Sep. 6, 2022

(54) SYSTEMS AND METHODS FOR TREATMENT OF FUNGUS

(71) Applicant: ACCURE MEDICAL, LLC, Brookfield, WI (US)

(72) Inventor: Daniel W. Van Der Weide, Madison, WI (US)

(73) Assignee: ACCURE MEDICAL, LLC, Brookfiled, WI (US)

( * ) Notice: Subject to any disclaimer, the term of this patent is extended or adjusted under 35 U.S.C. 154(b) by 982 days.

(21) Appl. No.: 16/082,146

(22) PCT Filed: Mar. 3, 2017

(86) PCT No.: PCT/US2017/020659
§ 371 (c)(1),
(2) Date: Sep. 4, 2018

(87) PCT Pub. No.: WO2017/152049
PCT Pub. Date: Sep. 8, 2017

(65) Prior Publication Data
US 2019/0054309 A1    Feb. 21, 2019

Related U.S. Application Data

(60) Provisional application No. 62/303,742, filed on Mar. 4, 2016.

(51) Int. Cl.
*A61N 5/02*       (2006.01)
*A61N 5/04*       (2006.01)
(Continued)

(52) U.S. Cl.
CPC .............. *A61N 5/025* (2013.01); *A61B 18/14* (2013.01); *A61F 7/00* (2013.01); *A61N 1/0468* (2013.01); *A61N 5/04* (2013.01); *A61B 18/1815* (2013.01); *A61B 2018/0066* (2013.01); *A61B 2018/00452* (2013.01); *A61B 2018/00642* (2013.01); *A61B 2018/00708* (2013.01); *A61B 2018/00797* (2013.01); *A61F 2007/0037* (2013.01);
(Continued)

(58) Field of Classification Search
CPC ... A61N 5/025; A61N 5/04; A61F 2007/0088; A61B 2018/00452
See application file for complete search history.

(56) References Cited

U.S. PATENT DOCUMENTS 7,824,395 B2    11/2010   Chan et al.
2008/0058782 A1   3/2008   Frangineas et al.
(Continued)

FOREIGN PATENT DOCUMENTS

WO    WO 2007027620 A1    3/2007
WO    WO 2017152049 A1    9/2017

OTHER PUBLICATIONS

International Search Report and Written Opinion of Related PCT/US2017/020659, dated Jul. 3, 2017, 18 pages.
(Continued)

*Primary Examiner* — Kaitlyn E Smith
(74) *Attorney, Agent, or Firm* — Casimir Jones, S.C.

(57) ABSTRACT

Provided herein are systems, devices and methods for the treatment of fungus. In particular, provided herein are systems, devices and methods employing energy to nail and tissue structures to treat fungal infection.

15 Claims, 2 Drawing Sheets

(51) Int. Cl.
- *A61N 1/04* (2006.01)
- *A61B 18/14* (2006.01)
- *A61F 7/00* (2006.01)
- *A61B 18/00* (2006.01)
- *A61B 18/18* (2006.01)

(52) U.S. Cl.
CPC ............... *A61F 2007/0046* (2013.01); *A61F 2007/0088* (2013.01); *A61F 2007/0096* (2013.01)

(56) References Cited

U.S. PATENT DOCUMENTS

| | | |
|---|---|---|
| 2008/0076958 A1 | 3/2008 | Britva et al. |
| 2009/0012515 A1 | 1/2009 | Hoenig et al. |
| 2011/0015549 A1 | 1/2011 | Eckhouse et al. |
| 2019/0321091 A1* | 10/2019 | Zemel ............... A61B 18/042 |

OTHER PUBLICATIONS

Choi et al., "Compact mixer-based 1-12 GHz reflectometer" IEEE Microwave and Wireless Components Letters, vol. 15, No. 11, pp. 781-783, Nov. 2005.

Paugam et al., "Comparison of real-time PCR with conventional methods to detect dermatophytes in samples from patients with suspected dermatophytosis" J. Microbiol. Methods, 95(2):218-222, Nov. 2013.

* cited by examiner

SYSTEMS AND METHODS FOR TREATMENT OF FUNGUS

The present application is a 371 U.S. National Phase Entry of pending International Application No. PCT/US2017/020659, filed Mar. 3, 2017, which claims priority to U.S. Provisional Patent Application Ser. No. 62/303,742, filed Mar. 4, 2016, the disclosure of which are herein incorporated by reference in their entireties.

FIELD

Provided herein are systems, devices and methods for the treatment of fungus. In particular, provided herein are systems, devices and methods employing energy to nail and tissue structures to treat fungal infection.

BACKGROUND

Nail fungus, also known as onychomycosis or tinea unguium, is a common infection that often begins as a discolored spot under the tip of a fingernail or toenail. As the infection progresses, nail fungus causes the nail to discolor, thicken and crumble at the edge. Nail fungal infections are typically caused by a dermatophyte fungus. Yeasts and molds also can be responsible for nail fungal infections.

Signs of nail fungus include thickened, brittle, crumbly, or ragged nails that are distorted in shape and white or yellow in color. Infected nails also may separate from the nail bed, a condition called onycholysis. A severe case of nail fungus can be painful and may cause permanent damage to the nails. Nail fungus may lead to other serious infections that spread beyond the hands or feet, particularly for those with a suppressed immune system due to medication, diabetes or other conditions.

Risk factors for infection of the nail by fungus include having a family history of onychomycosis, having athlete's foot, heavy perspiration, wearing footwear that hinders ventilation, living with someone that has nail fungus, being exposed to damp communal areas, and working in humid or moist environments. The risk of onychomycosis increases with increasing age and is more common in males than females. Other factors that predispose to nail fungal infection include having recent nail injury, psoriasis or other nail disorders, circulation problems, weakened immune system, or Down syndrome.

Existing treatments are highly unsatisfactory even though over a billion dollars a year is spent on oral and topical prescriptions. Oral antifungal drugs include terbinafine (LAMISIL) and itraconazole (SPORANOX). The drugs are typically taken for six to twelve weeks and results, if achieved, take months to observe. Treatment success rates with these drugs appear to be lower in adults over age 65. Importantly, oral antifungal drugs can cause serious side effects ranging from skin rash to liver damage. As such, these drugs may be contraindicated for patients with liver disease or congestive heart failure or those taking certain medications. Available topical treatments include medicated nail polishes (e.g., ciclopirox, aka PENLAC) and liquids (efinconazole, aka JUBLIA). The effectiveness of these treatments is limited.

Surgical and laser- and light-based approaches have also been used. Surgical approaches include nail removal. This is a painful procedure requiring weeks of dressing changes and management with pain medication. A new nail grows back very slowly (typically 12-18 months for a new big toenail) and may be permanently abnormal in shape and thickness. Laser and light approaches are newer and have not demonstrated effectiveness in curing nail fungus. They are also not available everywhere, are expensive, painful and typically not covered by insurance.

People have also attempted home remedies, which have limited to no effectiveness. These include over-the-counter antifungal nail creams and ointments, use of VICKS VAPORUB, personal mechanical trimming or thinning of nails, use of snakeroot extract, and use of tea tree oil.

In summary, no broadly effective treatment has been identified to address this common and significant public health concern. The most effective approaches to date have potential serious side effects including liver failure. New solutions are needed to the unsolved problem.

SUMMARY

Provided herein are systems, devices and methods for the treatment of fungus. In particular, provided herein are systems, devices and methods employing energy to nail structures or other keratinized surfaces to treat fungal infection. While toe and finger nails are illustrated herein, it should be understood that the systems, devices, and methods may be used with any keratinized tissue, including skin and hair.

In some embodiments, a system is provided. In some embodiments, the system comprises an energy source (e.g., generator) and an energy delivery device (e.g., comprising an antenna that emits energy when attached to said energy source). In some embodiments, the energy source is a radio-frequency (e.g., microwave) generator.

In some embodiments, the energy delivery device is configured to attach to or fit around an appendage (e.g., toe, finger) of a subject. In some embodiments, the device has an attachment component having top and bottom portions configured to receive an appendage (e.g., toe) therebetween. For example, in some embodiments, the attachment component is a clip with a top portion fitting above an appendage and a bottom portion fitting below an appendage. In some embodiments, the attachment component comprises a sheath that fits around the appendage. In some embodiments, the device is configured to receive multiple appendages simultaneously.

In some embodiments, the antenna is positioned in the device on the top portion side such that it is positioned above a nail when an appendage is received in the device. In some embodiments, the device comprises one or more dielectric layers. In some embodiments, the device has a dielectric layer below the antenna (e.g., positioned such that it directly makes contact with a toenail when a toe is received in the device). In some embodiments, an additional layer (e.g., sterile film, etc.) is positioned between this dielectric layer and the nail.

In some embodiments, one or more dielectric layers are positioned above the antenna (i.e., between the antenna and the top portion of the attachment component). In some embodiments, the one or more dielectric layers include one or more or all of: a first dielectric layer above the antenna (e.g., of similar or identical material and dimension to the dielectric layer below the antenna); a nail like dielectric layer (e.g., toenail like) above the first dielectric layer (e.g., dimensioned to mimic a toenail; and of the same or different material as the first dielectric layer); and a nail-bed like dielectric layer (e.g., dimensioned to mimic a nail bed; and of the same or different material as the first dielectric layer and/or toenail like dielectric layer).

In some embodiments, the device further comprises one or more thermal sensors. In some embodiments, the thermal sensors are located within the nail bed like dielectric material. In some embodiments, the system comprises a temperature monitoring component that at intervals or in real-time or near real-time monitors temperature and notifies a user of the temperature or automatically manages energy delivery (e.g., lowering delivery, shutting off energy, increasing delivery) in response to undesired temperatures.

In some embodiments, the system comprises a user interface. In some embodiments, the user interface comprises a computer processor, software, and a display that allow the user to select system parameters and to receive feedback during a procedure.

Devices comprising any of the system components are further provided herein.

Use of such devices or system (e.g., to treat toenail fungus) are also provided herein.

In some embodiments, provided herein are methods of treating an appendage (e.g., toe, finger) having nail fungus, comprising: attaching an energy delivery device comprising an antenna to the appendage and delivering energy to a nail bed of the appendage. In some embodiments, the device/system is configured to deliver energy substantially to the nail bed, such that delivered energy kills or inhibits the growth of toenail fungus causing organisms without damaging or harming tissue of the appendage or damaging or harming the nail.

In some embodiments, killing of toenail fungus causing organisms comprises at least a 20% (e.g., 30%, 40%, 50%, 60%, 70%, 80%, 90%, 95%, etc.) reduction in organism. Any suitable assay may be employed to measure organisms, including but not limited to, molecular techniques, culturing, and microscopy (see e.g., Paugam et al., J. Microbiol. Methods, 95(2):218-222 (2013), herein incorporated by reference in its entirety).

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
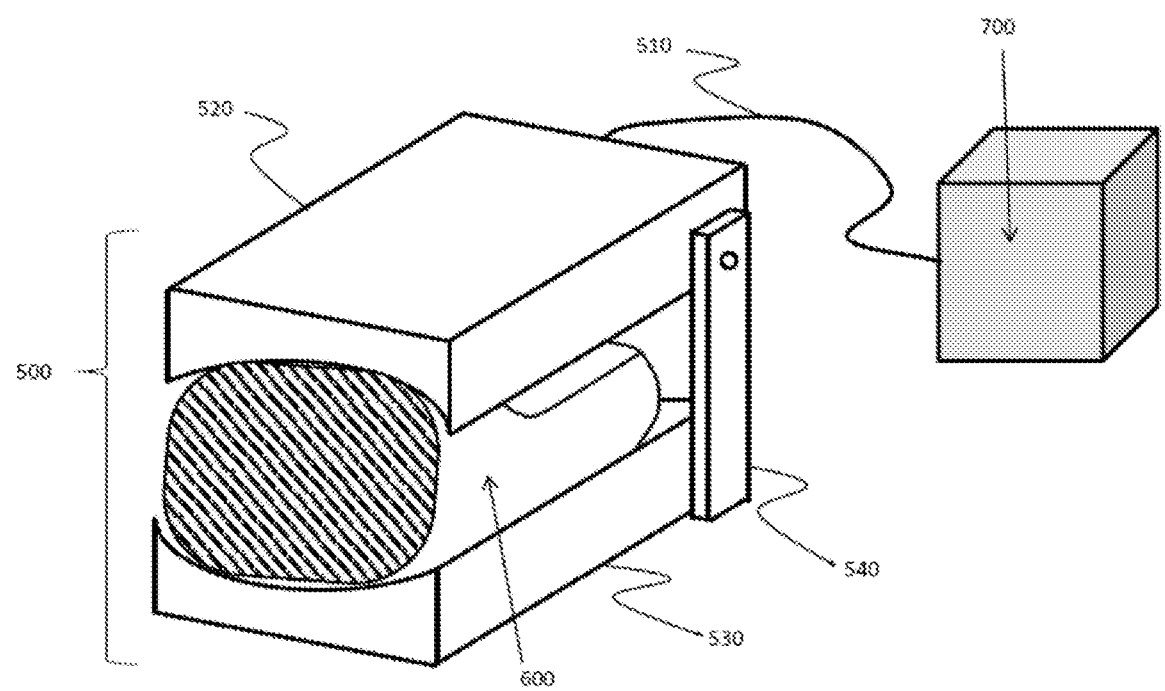
FIG. 1 is a schematic diagram of a nail fungus treatment system according to an embodiment of the present disclosure.

Provided herein are systems, devices and methods for the treatment of fungus. In particular, provided herein are systems, devices and methods employing energy to nail and tissue structures to treat fungal infection.

Any type of fungus or fungal infected tissue or nail may be treated by the systems, devices, and methods described herein. In some embodiments, the nail is on an appendage such as a toe or finger (i.e., toenails or finger nails). In some embodiments, the nail is treated at an early stage of fungal infection or prophylactically prior to infection. In some embodiments, the nail is treated at any various stage of infection, including severe infections where significant nail damage has already occurred.

In some embodiments, the treated subject is a human. However, the systems, devices, and methods find use in veterinary application for treatment of companion animals (e.g., dogs, cats), livestock (e.g., including treatment of fungal infections in hooves or surrounding tissue, zoo animals, wild animals, and the like). Human subjects include both adults and children. Human may be selected based on risk factors, including but not limited to age, heavy perspiration, being male, family history, working in humid or moist environments, wearing footwear that hinders ventilation, living with someone that has nail fungus, exposure to damp communal areas, having athlete's foot, having skin or nail injury, having psoriasis, circulation problems, weakened immune system, or Down syndrome.

The energy delivery provides a mechanism that is able to kill and/or inhibit the growth of a wide variety of organisms associated with nail fungus, onychomycosis, or related conditions. In some embodiments, the targeted organism is a dermatophyte (e.g., *Trichophyton rubrum*, *T. interdigitale*, *Epidermophyton floccosum*, *T. violaceum*, *Microsporum gypseum*, *T. tonsurans*, *T. soudanense*), *Candida*, or a non-dermatophytic mold (*Neoscytalidium*, *Scopulariopsis*, and *Aspergillus*), or combinations thereof.

Treatment times and intervals may be selected based on the subject's needs. In some embodiments, one treatment is provided. In some embodiments, two or more treatments are provided (e.g., 2, 3, 4, 5, 6, 7, 8, 9, 10, 11, 12, . . . , 20, . . . chronic). Treatments may be spaced apart by minutes, hours, days, weeks, months, or years.

In some embodiments, the result of treatment is partial to complete clearance of infection (e.g., greater than 10%, 20%, 30%, 40%, 50%, 60%, 70%, 80%, 90%, 95%, 98%, 99% clearance or reduction as measured by any suitable assay, including but not limited to, culture, KOH prep, calcofluor white stain, molecular tests, antigen testing, nail surface appearance, nail lost regrowth, etc.).

In some embodiments, there is minimal loss (e.g., no reversible loss) to no loss of healthy tissue, nail plate, or nail bed in response to the energy delivery.

In some embodiments, the energy delivery is combined with other existing therapies as a combination therapy. Such therapies include, but are not limited to, oral antifungal drugs (e.g., terbinafine, itraconazole), topical treatments (e.g., ciclopirox), mechanical treatments, and surgical and laser treatments.

Particular embodiments of the present disclosure are described herein below with reference to the accompanying drawings. In the following description, well-known functions or constructions are not described in detail to avoid obscuring the present disclosure in unnecessary detail.

FIG. 1 shows an energy delivery system comprising an energy delivery device 500 connected by a cable 510 to an energy source 700. In some embodiments, the energy delivery source 700 is a radio-frequency (RF) generator (e.g., a microwave generator). The energy source may comprise or consist of a tunable or fixed-frequency oscillator (either general-purpose laboratory-grade, e.g. from Keysight Technologies or Anritsu) or dedicated. Output powers from such oscillators may range from −20 dBm to +20 dBm or more, and frequency ranges may extend from 0.01 GHz to 20 GHz or more. Power from the oscillator may be amplified by a suitable solid-state power amplifier having gain of 1-20 dB or more and output power of +10 dBm to +40 dBm (e.g., 10 Watts) or more. The power amplifier may be a commercially-available module or a customized single- or multi-transistor module preferably located on or near to the applicator to minimize the effect of power losses in the delivery.

In some embodiments, the cable 510 is a coaxial cable. In some embodiments the cable 510 is a plurality of cables either separate or bundled together or integrated (i.e., two functionalities in the same housing). In some embodiments, the cable provides a coolant channel to circulate coolant to the energy delivery device. In such embodiments, a coolant source (e.g., liquid coolant, gas such as $CO_2$) is provided (not shown). In some embodiments, the cable further comprises a transmission line for transmitting data or other information to and from the energy delivery device to and from a control computer or component (not shown).

In some embodiments, the energy delivery device 500 has a top portion 520 and a bottom portion 530. The top portion 520, when the device is contacted with an appendage (e.g., toe or finger) 600 sits above the nail of the appendage. The bottom portion 530 is below the appendage. In some embodiments, the top portion 520 and bottom portion 530 are connected by a connector 540. The connector 540 may take any form that connects the top portion 520 and bottom portion 530. As shown in FIG. 1, the connector 540 attaches at a lower end to the bottom portion 530 and at a top end to the upper portion 520. Multiple connectors may be employed. The connector may include a spring or other tensioning component that causes the top portion 520 and bottom portion 530 to be directed towards one another by a force, such that the device clamps onto an object (e.g., finger, toe) inserted thereinbetween. Where such force is applied, the connector 540 may employ any of a variety of mechanisms employing clips or clamps, including, but not limited to, tension/extension springs, compression springs, torsion springs, constant springs, variable springs, coil springs, flat springs, machined springs, serpentine springs, cantilevers, leaf springs, bands, band clamp, bar clamp, C-clamp, set screw, spring clamp, and the like.

Figure 2:
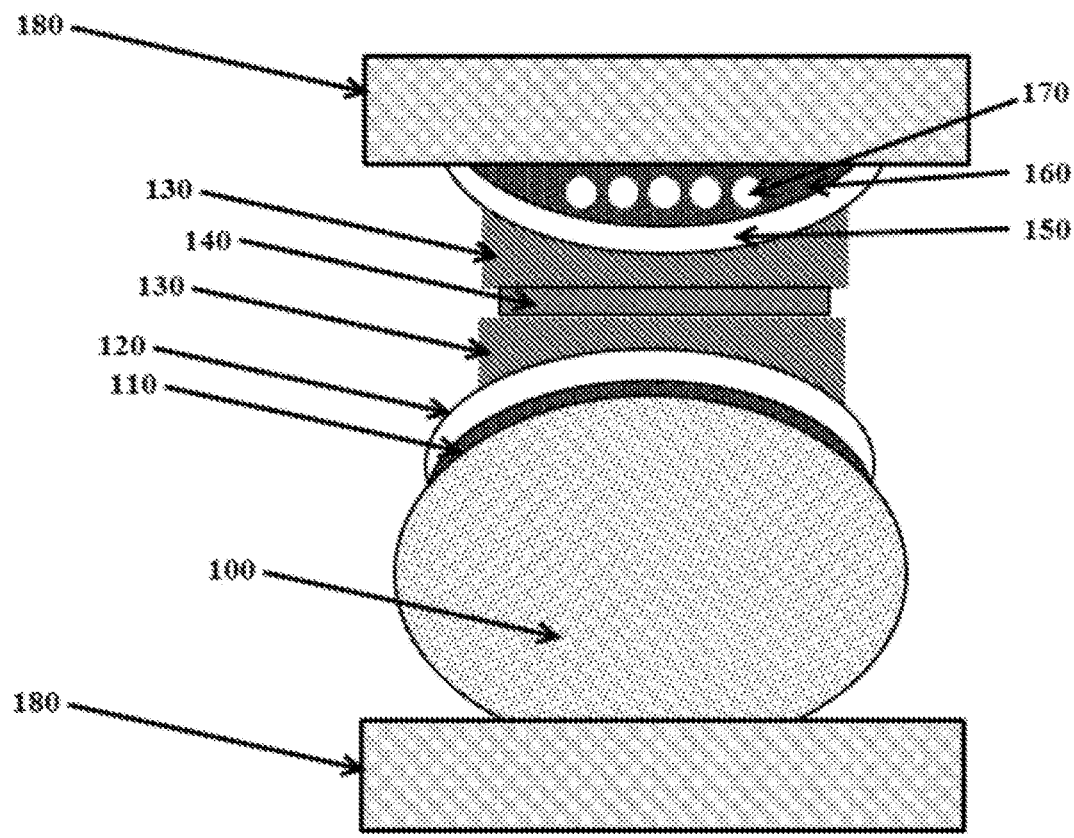
FIG. 2 is a schematic diagram of a nail fungus treatment device according to an embodiment of the present disclosure.

FIG. 2 shows an exemplary energy delivery device 500 in a cross-sectional view. The upper and lower portions are presented as a clip 180 on either side of a toe 100 (shown from an end view) having a nailbed 110 and toenail 120. The upper portion of the energy delivery device has an antenna 140 with a conformal dielectric material 130 below it (on the toenail side) and above it (on the clip side). The device further has a toenail-like dielectric material 150 above the conformal dielectric material (here dimensioned similar to the toe nail) and a nailbed-like dielectric material 160 above the toenail-like dielectric material 150. Also shown are a plurality of thermal sensors 170.

The antenna 140 is preferably comprised of a foil or thin conductor (Cu, Al, Au-plated Cu) formed in a single- or multi-resonant slot or bowtie configuration on a suitable dielectric substrate (Teflon, Kapton, FR-4, polyethylene). However, other types of antennas such as dielectric antenna may also be employed.

The conformal dielectric material 130, in some embodiments, may be a gel, silicone, PDMS, or other suitable material with low dielectric losses to maximize transfer of energy into the treatment zone.

A nail-like (e.g., toenail-like) dielectric material is combined with a nailbed-like dielectric material to form a tissue phantom that mimics the properties of the treatment zone. Embedded temperature sensors in this phantom treatment zone are thus able to witness and estimate the temperature in the treatment zone (achieved via energy deposition).

The toenail-like dielectric material 150, in some embodiments, may comprise or consist of FR-4, Kapton, polyethylene, Teflon, or the like, fashioned into dimensions similar to that of the nail under treatment.

The nailbed-like dielectric material 160, in some embodiments, may comprise or consist of silicone, PDMS, gel, or other tissue-like material with dielectric properties (e.g. water content) and dimensions similar to that of the nailbed.

Any type or number of temperature sensors 170 may be employed. In some embodiments, no sensor is employed. In some embodiments, a single sensor is employed. In some embodiments, two or more sensors are employed. The sensors may be wireless or wired and may employ any sensing mechanism. Contemplated sensors include, but are not limited to, thermistors, thermocouples, resistance thermometers, silicon bandgap temperature sensor, and the like. In some embodiments, sensors measure indirect consequences of temperature changes, such as pressure (e.g., pressure sensors) or displacement changes (e.g., due to swelling), for example, by assessing tension or displacement on a spring clip holding the treatment device onto a digit. In some embodiments, a reflectometer is employed. In some such embodiments, application of power is alternated between treatment and sensing of local dielectric properties of the treatment zone, enabling localized sensing of treatment progress (see e.g., Choi et al., Compact mixer-based 1-12 GHz reflectometer, in *IEEE Microwave and Wireless Components Letters*, vol. 15, no. 11, pp. 781-783, November 2005, herein incorporated by reference in its entirety).

In use, the energy delivery device is fitted onto or around an appendage or appendages to be treated. The generator is activated by a user or by a computer processor running a programmed treatment regimen. Energy is delivered to the energy delivery device from the generated to treat the tissue harboring the pathogen. In some embodiments, energy delivery comprises: a dose and schedule ranging from 0.1 W to 10 W or more, delivered in a variable-duty-cycle format for durations of 1 second to 3600 seconds or more, limited by the tissue temperature achieved in the treatment zone. In some embodiments, this treatment zone temperature is estimated by temperature sensors 170 disposed in a plane mirrored from the treatment zone by the antenna. Thus, as energy is deposited into the treatment zone, the symmetry of the antenna's power deposition pattern enables substantially equivalent power to be deposited into the treatment zone (typically the nail/nailbed interface). In some embodiments, the system adjusts energy delivery to achieve a desired heating temperature of the target tissue.

In some embodiments, a control computer is connected to the energy delivery device and the generator and provides a user interface for the user to control the system. In some embodiments, the control features include, but are not limited to: selecting an energy level or treatment time; selecting a pre-programmed energy delivery protocol; collecting procedure data (temperature, energy levels); collecting or inputting patient-specific data (e.g., name, medical history, images of treatment area, insurance provider, payment code; etc.); setting safety protocols; selecting manual versus automatic settings; controlling coolant flow; turning the energy delivery device or generator or control computer on or off; and the like.

The temperature for killing of pathogens is selected based on the context of the desired treatment, including the nature of the subject being treated and the pathogen to be killed. In some embodiments, target tissue comprising a pathogen is heated to a temperature from 30° C. to 70° C. for a desired period of time (e.g., 40° C. to 60° C.; 45° C. to 55° C.; 50° C. to 55° C.; or any ranges or individual temperatures therein between; e.g., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., etc.). Experiments conducted during the development of the technology, employing an onychomycosis model with plate-cultured *T. rubrum*, demonstrated significant growth delay and death of organism at temperatures of 52° C. and 54° C.

Additional experiments shows significant pathogen death when treated for longer time periods at 50° C., with increased killing at each 10 minute interval from 10 minutes through 90 minutes of treatment. Accordingly, in some embodiment, energy is provided to a nail bed to maintain a target temperature at the nail bed (e.g., 30° C. to 70° C.) for one or more minutes (e.g., 1 minute, 2 minutes, 5 minutes, 10 minutes, 20 minutes, 30 minutes, 40 minutes, 50 minutes, 60 minutes, 70 minutes, 80 minutes, 90 minutes, or longer, or any time ranges therein between). Regrowth was significantly prevented compared to controls that did not undergo temperature treatment (5% regrowth of sub-cultures (2 of 40) for 90 minute 50° C. treated cultures compared to 100% regrowth (28 of 28) of sub-cultures from untreated (zero minute) samples).

I claim:

1. A system comprising:
   a) an energy source; and
   b) an energy delivery device, said energy delivery device comprising:
      i) an appendage attachment component having top and bottom portions configured to receive an appendage therebetween;
      ii) an antenna electrically coupled to said energy source and positioned above a nail when said appendage attachment component receives an appendage;
      iii) a dielectric layer below said antenna;
      iv) a first dielectric layer above said antenna; and
      v) one or more additional dielectric layers above said first dielectric layer.

2. The system of claim 1, wherein said one or more additional dielectric layers comprise a toenail like dielectric layer and a nail-bed like dielectric layer.

3. The system of claim 1, further comprising one or more thermal sensors.

4. The system of claim 1, wherein said energy source is a radio-frequency energy generator.

5. The system of claim 4, wherein said radio-frequency energy generator is a microwave energy generator.

6. The system of claim 1, wherein said attachment component is a clip, wherein said top and bottom portions are connected by a tensioning component at a proximal end of said clip.

7. The system of claim 1, wherein said antenna comprises a foil or thin conductor formed in a single- or multi-resonant slot or bowtie configuration on a dielectric substrate.

8. The system of claim 1, further comprising a user interface.

9. The system of claim 8, wherein said user interface controls energy delivery from said energy source to said energy delivery device.

10. A device comprising:
    a) an appendage attachment component having top and bottom portions configured to receive an appendage therebetween;
    b) an antenna positioned above a nail when said appendage attachment component receives an appendage;
    c) a connector for electrically coupling said antenna to a radiofrequency energy source;
    d) a dielectric layer below said antenna;
    e) a first dielectric layer above said antenna; and
    f) one or more additional dielectric layers above said first dielectric layer.

11. The device of claim 10, wherein said one or more additional dielectric layers comprise a toenail like dielectric layer and a nail-bed like dielectric layer.

12. The device of claim 10, further comprising one or more thermal sensors.

13. A method of treating an appendage having nail fungus, comprising:
    a) attaching said device of claim 10 to said appendage; and
    b) delivering radio-frequency energy to a nail bed of said appendage using said device of claim 10.

14. The method of claim 13, wherein said radio-frequency energy comprises microwave energy.

15. The method of claim 13, wherein said energy kills nail fungus causing organisms without harming tissue of the appendage.

* * * * *